(12) United States Patent
Widlund et al.

(10) Patent No.: US 6,660,902 B2
(45) Date of Patent: Dec. 9, 2003

(54) ABSORBENT PRODUCT HAVING CONTINUOUS FIBERS BONDED IN A BONDING PATTERN

(75) Inventors: Urban Widlund, Pixbo (SE); Christina Steger, Mölndal (SE); Roy Hansson, Mölndal (SE); Sofia Roxendal, Pixbo (SE); Peter Wessel, Ytterby (SE)

(73) Assignee: SCA Hygine Products AB, Gothenburg (SE)

( * ) Notice: Subject to any disclaimer, the term of this patent is extended or adjusted under 35 U.S.C. 154(b) by 16 days.

(21) Appl. No.: 09/328,899

(22) Filed: Jun. 9, 1999

(65) Prior Publication Data

US 2002/0087136 A1 Jul. 4, 2002

Related U.S. Application Data

(63) Continuation of application No. PCT/SE98/02215, filed on Dec. 3, 1998.

(30) Foreign Application Priority Data

Dec. 3, 1997 (SE) ................................................ 9704484

(51) Int. Cl.⁷ ................................................ A61F 13/15
(52) U.S. Cl. ........................ 604/365; 604/366; 604/378; 604/380
(58) Field of Search ................................ 604/380, 382, 604/378, 365, 374, 366, 383, 384, 385.23, 385.01, 379

(56) References Cited

U.S. PATENT DOCUMENTS

| | | | | |
|---|---|---|---|---|
| 3,371,667 A | | 3/1968 | Morse | 128/290 |
| 4,360,022 A | * | 11/1982 | Usami et al. | 128/290 |
| 4,676,786 A | * | 6/1987 | Nishino | 604/378 |
| 5,382,245 A | | 1/1995 | Thompson et al. | 604/367 |
| 5,613,962 A | | 3/1997 | Kenmochi et al. | 604/378 |
| 5,662,633 A | * | 9/1997 | Doak et al. | 604/378 |
| 5,695,486 A | * | 12/1997 | Broughton et al. | 604/374 |
| 5,700,254 A | * | 12/1997 | McDowall et al. | 604/378 |

FOREIGN PATENT DOCUMENTS

| | | | | |
|---|---|---|---|---|
| EP | 312 118 | 4/1989 | | A61F/13/18 |
| EP | 391 814 | 10/1990 | | A61F/13/15 |
| EP | 0 596 191 | 5/1994 | | |
| EP | 0 674 891 | 10/1995 | | A61F/13/15 |
| EP | 685 214 | 12/1995 | | A61F/13/15 |
| EP | 686 384 | 12/1995 | | A61F/13/15 |
| FR | 2 713 083 | 6/1995 | | A61F/13/46 |
| GB | 2 209 672 | 5/1989 | | A61F/13/18 |
| WO | 90/14814 | 12/1990 | | A61F/13/46 |
| WO | 93/09745 | 5/1993 | | A61F/13/46 |
| WO | 95/00095 | 1/1995 | | A61F/13/15 |
| WO | 96/00550 | 1/1996 | | A61F/13/15 |

OTHER PUBLICATIONS

The Nonwven Fabrics Handbook, Starr, John R. Inc. , Association of the Nonwoven Fabrics Industry.*

* cited by examiner

*Primary Examiner*—Weilun Lo
*Assistant Examiner*—Jacqueline F Stephens
(74) *Attorney, Agent, or Firm*—Burns, Doane, Swecker & Mathis, LLP

(57) ABSTRACT

Absorbent article such as a diaper, pant diaper, incontinence guard, sanitary napkin, wound dressing or the like comprising a layer of continuous fibers (9), so called tow, which is bonded in points, spots or lines in a bonding pattern (10), but where the fibers otherwise are substantially unbonded to each other. The layer can either be used as a liquid acquisition layer (5) in the article under the topsheet (2), as a topsheet (12) or as a combined topsheet and liquid acquisition layer (22).

20 Claims, 4 Drawing Sheets ns filed on Dec. 3 1998
ABSORBENT PRODUCT HAVING CONTINUOUS FIBERS BONDED IN A BONDING PATTERN This application is a continuation of PCT International Application No. PCT/SE98/02215, filed on Dec. 3, 1998, and which designated the United States of America.

TECHNICAL FIELD

The present invention refers to an absorbent article such as a diaper, pant diaper, incontinence guard, sanitary napkin, wound deressing or the like of the kind comprising a liquid permeable topsheet, a liquid impervious backsheet and an absorbent body arranged therebetween.

BACKGROUND OF THE INVENTION

Absorbent articles of the above mentioned kind are intended to absorb body liquids such as urine and blood. They usually comprise a liquid pervious topsheet, intended to be facing the wearer during use, in the form of a nonwoven material for example a spunbond material. It is also known to incorporate a liquid acquisition layer between the topsheet and the absorbent body, said liquid acquisition layer having the ability to quickly receive large amounts of liquid, to distribute it and temporarily store it before it is absorbed by the underlying absorbent body. This is important especially in today's thin compressed absorbent bodies often with a high amount of so called superabsorbents, which have a high absorption capacity but in many cases a too low absorption speed in order to momentaneously be able to absorb the large amount of liquid that can be discharged during a few seconds at urination.

A porous relatively thick acquisition layer, for example in the form of a fibrous wadding, a carded fibrous web or other type of fibrous material has a high momentaneous liquid receiving capacity and can temporarily store liquid before it is absorbed by the absorbent body. The same applies for porous foam materials. The liquid is then drained succesivley to the underlying absorbent body, after which the acquisition layer again has capacity to receive liquid from a repeated wetting.

Examples of absorbent articles comprising such porous acquisition layer are for example disclosed in U.S. Pat. No. 3,371,667, EP-A-0,312,118 and EP-A-0,474,777.

The materials used today as acquisition layers in absorbent articles are mostly functioning well but are relatively expensive and can sometimes have an insufficient acquisition time, especially at the second and third wettings if large amounts of liquid are involved.

It is previously known through EP-A-0,391,814 and GB-B-2,209,672 to use continuous nonbonded synthetic fibers, so called tow, in absorbent articles to spread liquid in the longitudinal direction of the article.

Another problem is that conventional liquid pervious topsheet materials used for absorbent articles of this kind, usually a nonwoven material of synthetic fibers, e g a spunbond material, often has a lower acquisition rate for liquid than the acquisition layer, at which liquid can leak from the article before it reaches the acquisition layer. The problem can of course be solved by using a topsheet material which is very open and by that has a high liquid permeability. Such an open topsheet material can however cause problems with a too low strength and sharp fiber ends from the acquisition layer may penetrate the open topsheet material and irritate the user.

OBJECT and MOST IMPORTANT FEATURES of the INVENTION

The object of the present invention is to provide a material having a high acquisition rate for liquid also at repeated wettings, has a high strength and wear resistance, high comfort and can be produced at a low cost. This has according to the invention been provided by a layer of continous fibers, so called tow, which is bonded in points, spots or lines in a bonding pattern, but where the fibers otherwise are substantially unbonded to each other.

The material layer can be used as a liquid acquisition layer under a topsheet material, as a topsheet material or as an integrated topsheet/liquid acquisition layer.

DESCRIPTION OF THE DRAWINGS

The invention will below be closer described with reference to some of the embodiments shown in the accompanying drawings.

DESCRIPTION OF EMBODIMENTS

Figure 1:
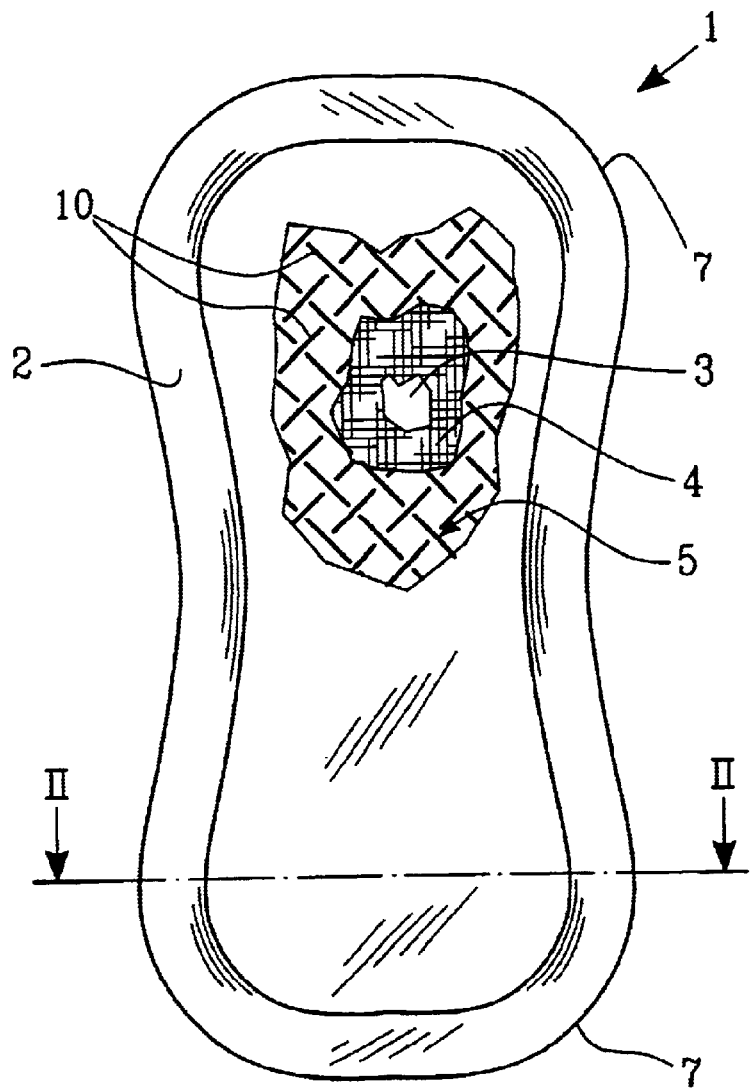
FIG. 1 is a plan view of an absorbent article in the form of an incontinence guard.
Figure 2:
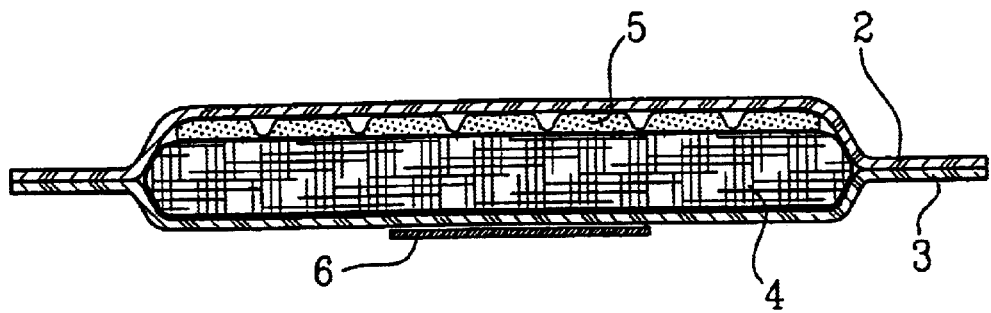
FIG. 2 is a section according to the line II—II in FIG. 1.

FIGS. 1 and 2 show schematically an example of an incontinence guard 1 comprising a liquid pervious topsheet 2, a liquid impervious backsheet 3 and a absorbent body 4 enclosed therebetween. A porous resilient liquid acquisition layer 5 is arranged between the liquid pervious topsheet 2 and the absorbent body 4.

The liquid pervious topsheet 2 can comprise a nonwoven material, for example a spunbond material of synthetic filaments, a meltblown material, a thermobonded material or a bonded carded fibrous material. The liquid impervious backsheet 3 can consist of a plastic film, a nonwoven material which is coated with a liquid impervious material or a hydrophobic nonwoven material which resists liquid penetration.

The topsheet 2 and the backsheet 3 have a larger surface area than the absorbent body 4 and the liquid acquisition layer 3 and extend outside the edges thereof. The layers 2 and 3 are interconnected within the projecting portions, for example by gluing or welding with heat or ultrasonic.

The absorbent body 4 can be of any conventional kind. Examples of common absorption materials are cellulosic fluff pulp, tissue layers, highly absorbent polymers (so called superabsorbents), absorbent foam materials, absorbent nonwoven materials and the like. It is common to combine cellulosic fluff pulp with superabsorbents in an absorbent body. It is also common to have absorbent bodies comprising layers of different materials with different properties concerning liquid acquisition capacity, liquid distribution capacity and liquid storage capacity. This is wellknown for the person skilled in the art and need not be described in detail. The thin absorbent bodies which are common in for example baby diapers and incontinence guards often consist of a compressed mixed or layered structure of cellulosic fluff pulp and superabsorbent.

On the outside of the liquid impervious backsheet 3 fastening means in the form of strips 6 of a selfadhesive glue are arranged. An incontinence guard of the kind shown in FIG. 1 is mainly intended to be used by persons suffering from a relatively light incontinence and is easily worn in ordinary underpants. The fastening means 6 serve to keep the incontinence guard in place in the underpants during use. A number of other types of glue patterns, for example transverse, are of course possible as well as other types of fastening means such as hook and loop, snap fasteners, girdles, special underpants or the like.

An incontinence guard of the kind disclosed in FIG. 1 is mainly intended to be used by persons suffering from relativley light incontinence and can easily be worn in a pair of ordinary underpants. The fastening means 6 serves to keep the incontinence guard in place during use.

The incontinence guard is hour glass shaped with broader end portions 7 and a more narrow crotch portion 8 located between the end portions. The crotch portion 9 is the portion of the incontinence guard that is intended during use to be worn in the crotch between the legs of the wearer and serve as a receiving portion for the discharged body fluid.

Figure 3:
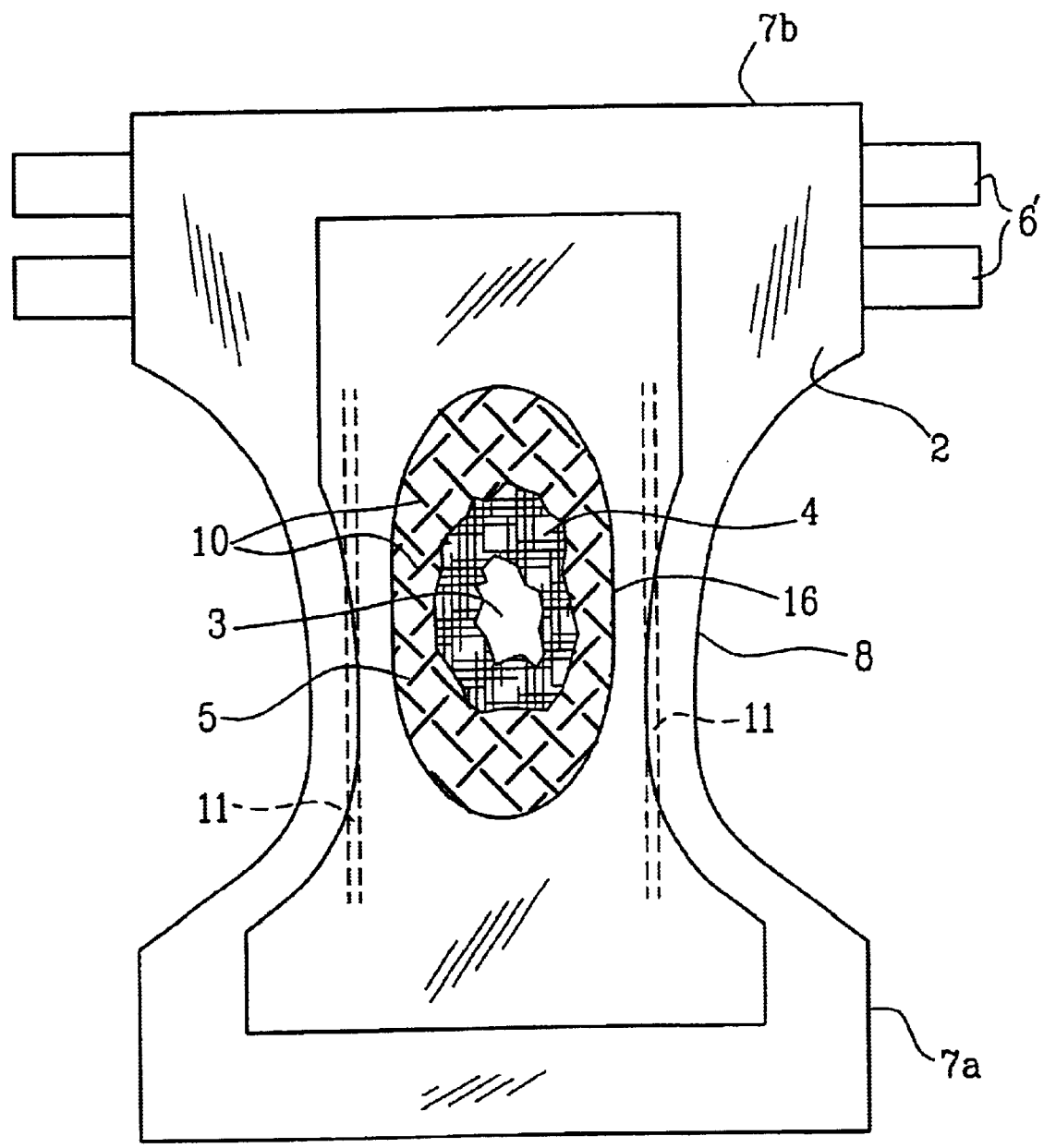
FIG. 3 is a plan view of an absorbent article in the form of a diaper.

In FIG. 3 there is shown an absorbent article in the form of a diaper which like the above described incontinence guard comprises a liquid pervious topsheet 2, a liquid impervious backsheet 3 and an absorbent body 4 enclosed therebetween and further an acquisition layer 5 applied between the topsheet 2 and the absorbent body 4. In the embodiment shown the topsheet is provided with a hole 16 opposite the intended wetting area, or which the acquisition layer 5 is exposed directly towards the user in this area. Instead of one hole 16 several smaller holes may be arranged.

The diaper is intended to enclose the lower part of the user's trunk as a pair of absorbent pants. It has a front portion 7*a* intended during use to be worn against the front part of the user's body, a back portion 7*b* intended during use to be worn against the back part of the user, and a therebetween a narrower crotch portion 8 intended to be worn in the crotch part between the legs of the user. In order to fasten the diaper together to the desired pant shape tape strips 6' around the waist of the wearer. Other fastening means such as hook and loop means (Velcro), hooks etc. are of course possible.

It should be noted that the incontinence guard and the diaper shown in the drawings and described above only are non-limiting examples of an absorbent article. Thus the shape of the article as well as the construction thereof can be varied. The absorbent article can also be a diaper, a pant diaper, a sanitary napkin or the like. The absorbent article can be disposable or reuseable. For reuseable articles other materials than the above described are however used as a liquid pervious topsheet and absorbent body respectively.

Between the liquid pervious topsheet 2 and the absorbent body 4 there is arranged a porous and resilient acquisition layer 5 having the ability to quickly receive large amounts of liquid and distribute the liquid and store it temporarily before it is absorbed by the underlying absorbent body 4. This ability should be essentially maintained also after wetting of the material. The acquisition layer 5 can either cover the entire absorbent body 4, extend outside thereof or cover only part of the central portions of the absorbent body.

According to the invention the acquisition layer 5 consists of a layer of continuous fibers 9, so called tow, which have been bonded together in points, spots or lines forming a bonding pattern 10, but otherwise are substantially unbonded to each other. In the embodiment shown in FIG. 1 the bonding pattern 10 is a pattern of lines with short lines arranged in a zigzag configuration. The bonding pattern is achieved by for example ultra sonic welding or other thermal bonding. Examples of other suitable thermal bonding methods are pattern calendering, laser bonding etc. This implies that at least some of the fibers in the tow are thermoplastic. Examples of thermoplastic fibers are polyolefines, polylactides, polyamides, polyester and the like. Also so called bicomponent fibers are included. As an alternative to thermobonding bonding can be made by a bonding agent through so called print bonding or dotbonding or mechanically through so called entangling by needling or by water jets. The choice of bonding type is mainly decided by which type of fibers are used in the tow.

The design of the bonding pattern 10 can of course vary within wide limits. The pattern may be in the form of points, spots or preferably lines. The lines may be straight as well as curved and the length can vary from a few millimeters to extending transversely or diagonally across the entire article. Preferably the lines extend across or obliquely across the longitudinal direction of the fibers 9, so that a plurality of fibers are bonded to each other by each bonding line. It is also an advantage if different bonding lines overlap each other as seen across the longitudinal direction of the fibers, so that a main part of the fibers are bonded at least at some part of their length.

The bonding pattern can be the same over the entire acquisition layer 5 or be different in different parts thereof, thus the bonding pattern can be more sparsely in the wetting area and tighter outside thereof. It is also possible to design the bonding pattern in such a way that the layer 5 will have different thickness in different parts of the, article, for example thinner in the central portions thereof and thicker in the surrounding edge portions in order to create a bowl shape which provides a liquid receiving volume, alternatively thicker in the central portions than in the surrounding edge portions in order to provide a better body contact.

Fiber tow is supplied in sacks or in the form of bales or rolls of continuous fibers, which either are straight, crimped or curled. Crimped or curled fibers are preferred in this case since they provide a very open and airy structure. The bales or the like are opened in special converting devices in which the fibers are separated from each other, stretched and spread out to an essentially evenly thick layer. The layer is bonded in the desired bonding pattern according to above and is cut in suitable lengths either before or after application in en absorbent article. The bonding can alternatively be made after cutting. A tow is a relativley cheap delivery form of fibers as compared to nonwoven, waddings or the like which are normally used as acquisition materials.

Figure 4:
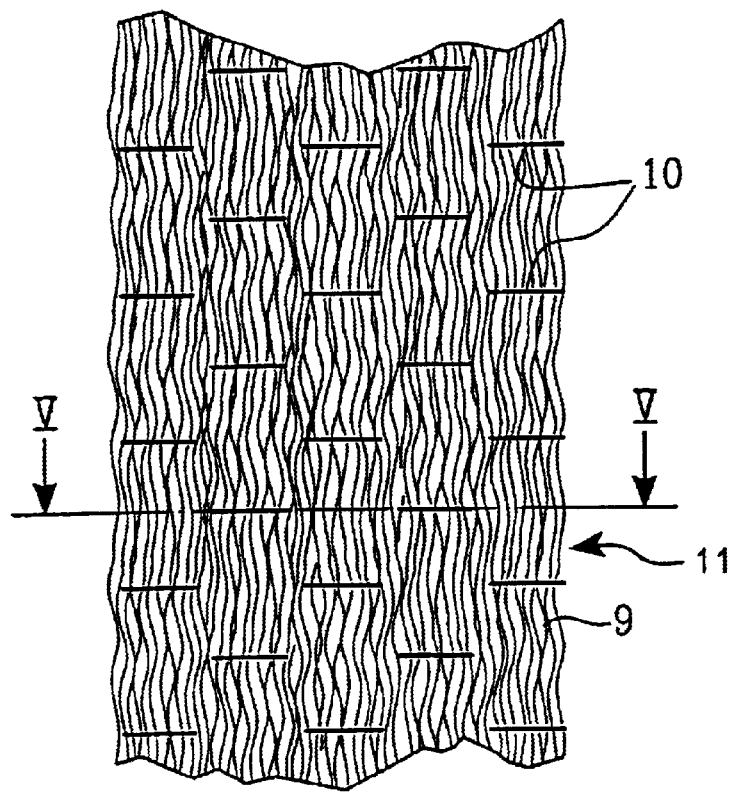
FIG. 4 shows schematically a piece of a fibrous material layer according to the invention.
Figure 5:
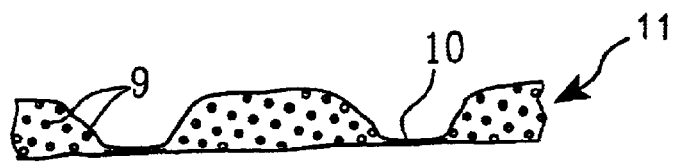
FIG. 5 shows on an enlarged scale a section according to the line IV—IV in FIG. 3.

In FIGS. 4 and 5 there are schematically shown a piece of a layer 11 of continuous fibers 9 which have been bonded in a simple bonding pattern 10 with transverse short lines. The fibers 9 are except at the bonding sites unbonded to each other.

The fibers in the tow can be of any suitable material such as polyethylene, polypropylene, polyamide, polyester, polylactide, polyvinyl acetate, cellulose acetate, regenerated cellulose such as viscose and rayon, or af bicomponent type with a shell of a polymer having a lower melting point and a core of a polymer having a higher melting point. In a bicomponent fiber the core which is not melted provides stiffness and resiliency while the shell provides bonding. Specially preferred are such fibers having a high resiliency, for example polyester, copolyester and polypropylene.

Figure 6:
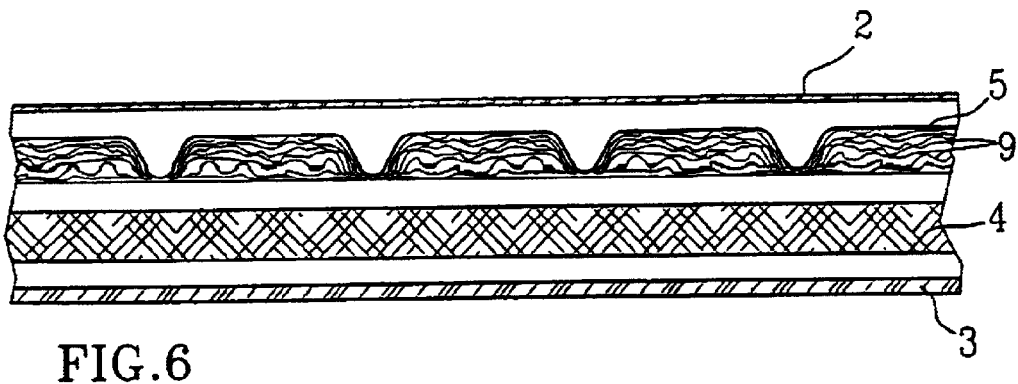
FIGS. 6–9 are schematic exploded cross-sectional view of four different embodiments of the article according to the invention.

The fiber thickness can vary but should be in the interval 0.5 to 50 dtex, preferably 1.5 to 25 and most preferably 2 to 15 dtex, if the material is to be used as an acquisition layer. The open airy structure in combination with the relatively coarse fiber dimension gives a very rapid liquid acquisition. Besides the material is strong due to the continuous fibers which provide strength in the longitudinal direction, and the bonding pattern which provides strength in the transverse direction In the above example the material has been used as an acquistion layer 5 under a liquid pervious topsheet 2. This is also shown in FIG. 6. The basis weight of the bonded fiber tow should in this case be at least 10 g/m$^2$, preferably in the interval 10–1000 g/m$^2$, more preferably 30–700 g/m$^2$ and most preferably 30–350 g/m$^2$. The topsheet 2 can be of any optional kind, but preferably has a relatively open structure which permits a quick liquid acquisition. The topsheet 2 may be bonded to the acquisition layer 5 in the bonding points 10.

Figure 7:
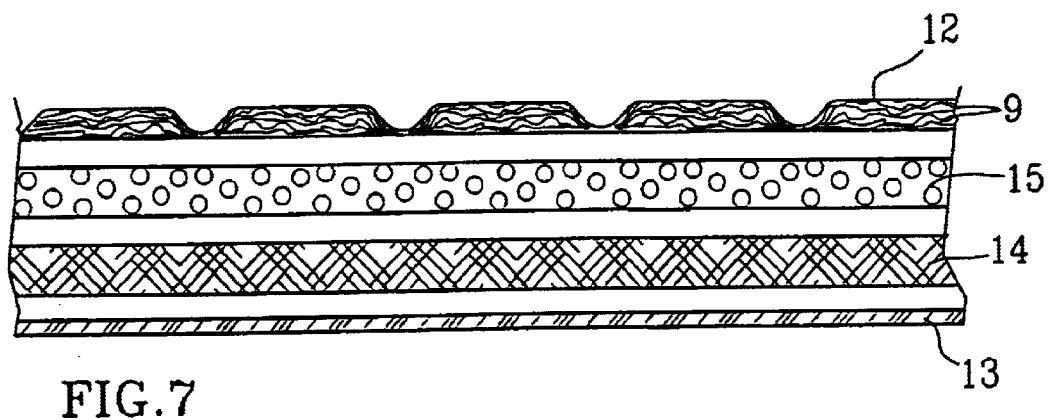

In FIG. 7 there is shown an alternative embodiment in which the bonded fiber tow according to the invention is used as a liquid pervious topsheet 12. The basis weight should in this case be at least 5 g/m$^2$, preferably in the interval 5–500 g/m$^2$ and more preferably 5–200 g/m$^2$ and the fiber thickness should be in the interval 0.5–50 dtex, preferably 1.5–25 and more preferably 2–15 dtex. In other respect the material can be the same as described above. Under the topsheet 12 there is arranged an acquisition layer 15 which may be of optional kind. The absorbent article according to FIG. 7 further comprises an absorbent body 14 and a liquid pervious backsheet 13.

Figure 8:
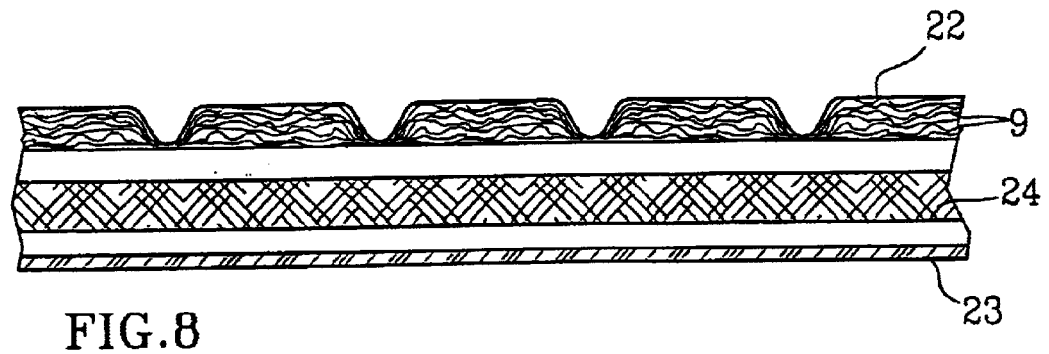

In the embodiment according to FIG. 8 the bonded fiber tow according to the invention has been used as a combined topsheet and acquisition material 22. The surface weight should in this case be at least 10 g/m$^2$, preferably in the interval 10–1000 g/m$^2$, more preferably 30–700 g/m$^2$ and most preferably 30–350 g/m$^2$ and the fiber thickness should be in the interval 0.5–50 dtex, preferably 1.5–25 and more preferably 2–15 dtex. The absorbent article according to FIG. 8 further comprises as usual an absorbent body 24 and a liquid pervious backsheet 23.

Figure 9:
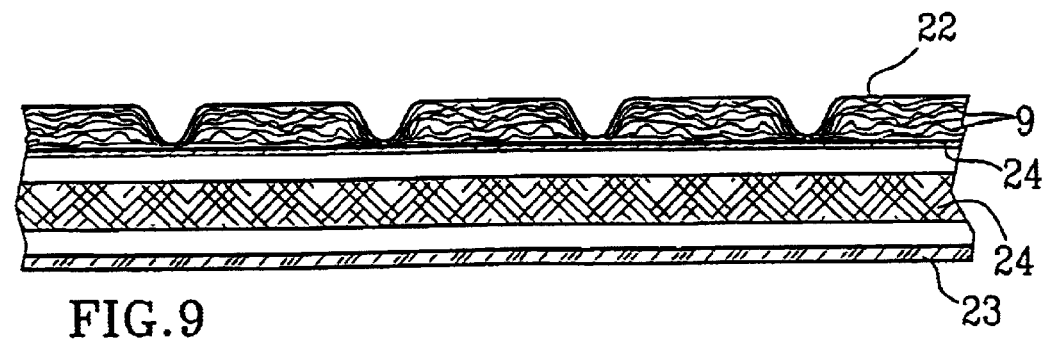

The embodiment according to FIG. 9 differs from the one disclosed in FIG. 8 by the fact that a support material 25 eg in the form of a nonwoven has been integrated on the underside of the combined topsheet/acquisition layer 22. Such a support material can of course alternativley or also be integrated to the upper side of the topsheet/acquisition layer 22 or to the acquisition layer 5 according to FIG. 6 or the topsheet 12 according to FIG. 7.

In the embodiments according to FIGS. 7–9 the bonded fiber tow according to the invention will be directly contacting the skin of the wearer. In this case there are high demands on the softness and comfort of the material. Since the material consists of continuous fibers there are no protruding sharp fiber ends which may irritate the skin, but the material is very soft and pliable. Besides it has a sufficient strength and wear resistance due to the longitudinal continuous fibers 9, which provide strength in the longitudinal direction, and the bonding pattern which provides strength in the transverse direction.

As was stated above it is preferred that crimped or curled fibers are used in the tow, since they provide an extra open and lofty structure. It is also possible to use a combination of straight and crimped or curled fibers.

It is also possible to use different kinds of fibers or different thicknesses of fibers in different parts of the tow, ie in different layers or zones thereof. By this it would be possible to create desired absorption patterns. It would also be possible to create gradients of different hydrophilicity and/or pore size. Superabsorbent fibers could also be admixed into the tow.

Acquisition Time

Comparative tests have been made to measure the acquisition time of absorbent articles, on one hand of a reference product in the form of a commercially available light incontinence product, on the other hand in the form of a test product, in which the topsheet and acquisition layer have been replaced by a bonded tow according to the invention. The topsheet in the reference product was a carded nonwoven having the basis weight 23 g/m$^2$ and the acquisition layer was a needled wadding having the basis weight 68 g/m$^2$. The absorbent core was the same in both the reference product and the test product and consisted of two layers, an upper layer in the form of a mixture of CTMP (chemothermomechanical pulp) and superabsorbent and a lower layer in the form of a mixture of chemical pulp and superabsorbent.

The bonded fiber tow which in the test product replaced the topsheet and the acquisition layer of the reference product consisted of polyester fibers of the thickness 6.7 dtex and the basis weight 70 g/m$^2$.

As test liquid there was used a synthetic urine ecording to the description i e g EP 0,565,606 and which can be obtained from Jayco Pharmaceuticals Co., Pennsylvania. The composition was 2 g/l KCl; 2 g/l Na$_2$SO$_4$; 0.85 g/l (NH$_4$)H$_2$PO$_4$; 0.15 g/l (NH$_4$)$_2$HPO$_4$; 0.19 g/l CaCl$_2$ and 0.23 g/l MgCl$_2$. The pH of the composition wasr 6.0–6.4.

Three addition each of 50 ml synthetic urine were made with an interval of 10 minutes. The time it took before all liquid was absorbed was measured (visual observation). The resultat is shown in the table below.

| Product | Acquisition time 1 (s) | Acquisition time 2 (s) | Acquisition time 3 (s) |
|---|---|---|---|
| Reference | 3.65 | 7.10 | 11.66 |
| Test | 3.35 | 5.29 | 6.64 |

As can be seen from this test the test product had a quicker acquisition time than the reference product. The difference was especially significant at the second and third wettings.

Figure 10:
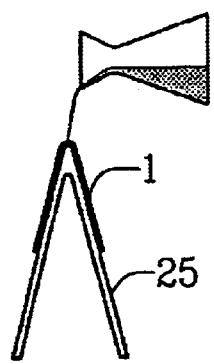
FIG. 10 is a schematic view of a device for demonstrating liquid acquisition of an absorbent article folded as it will be used in between the legs of the wearer.

In FIG. 10 there is schematically shown a simple device with which the excellent acquisition of an absorbent article according to the present invention can be easily demonstrated. The device comprises a stand 25 in the form of a pair of legs arranged at an acute angle to each other. The article 1 is longitudinally folded in a corresponding way it will be folded when placed in the crotch between the legs of the user, and is placed on the stand 25 in the folded condition. A test liquid in an amount of e g 50 ml is quickly poured on the article. A conventional absorbent article will likely leak and not be able to absorb all liquid quickly enough. An absorbent article according to the present invention on the other hand will be able to absorb liquid more quickly and the risk for leakage is considerably reduced.

What is claimed:

1. An absorbent article, the absorbent article comprising:
   a liquid permeable topsheet,
   a liquid impervious backsheet,
   an absorbent body arranged therebetween, and a layer of continuous filament fibers, which are bonded together in a bonding pattern, at least some of said fibers being thermoplastic and the bonding pattern being achieved by thermal bonding, with the bonds creating open spaces beneath the topsheet to allow for liquid distribution, wherein the bonding pattern comprises points, spots or lines which cross a longitudinal direction of the continuous filament fibers, and wherein different bonding lines overlap each other as seen in a transverse direction of the article, so that a main part of the filament fibers are bonded along at least a part of their length.

2. The absorbent article as claimed in claim 1, wherein the bonding pattern is nonrandom.

3. The absorbent article as claimed in claim 1, wherein the layer of continuous filament fibers is used as a liquid acquisition layer and is arranged between the topsheet and the absorbent body.

4. The absorbent article as claimed in claim 3, wherein the layer of continuous filament fibers has a basis weight of at least 10 g/m$^2$.

5. The absorbent article as claimed in claim 3, wherein the topsheet in the intended wetting area is provided with at least one opening through which the liquid acquisition layer is exposed towards the user.

6. The absorbent article as claimed in claim 3, wherein the layer of continuous filament fibers has a basis weight of about 10 to 1000 g/m$^2$.

7. The absorbent article as claimed in claim 3, wherein the layer of continuous filament fibers has a basis weight of about 30 to 700 g/m$^2$.

8. The absorbent article as claimed in claim 3, wherein the layer of continuous filament fibers has a basis weight of about 30 to 350 g/m$^2$.

9. The absorbent article as claimed in claim 1, wherein the layer of continuous filament fibers is used as an integrated topsheet/liquid acquisition layer.

10. The absorbent article as claimed in claim 9, wherein the layer of continuous filament fibers has a basis weight of at least 10 g/m$^2$.

11. The absorbent article as claimed in claim 9, wherein the layer of continuous filament fibers has a basis weight of about 10 to 1000 g/m$^2$.

12. The absorbent article as claimed in claim 9 wherein the layer of continuous filament fibers has a basis weight of about 30 to 700 g/m$^2$.

13. The absorbent article as claimed in claim 9, wherein the layer of continuous filament fibers has a basis weight of about 30 to 350 g/m$^2$.

14. The absorbent article as claimed in claim 1, wherein at least a part of the continuous filament fibers in said layer are crimped or curled.

15. The absorbent article as claimed in claim 1, further comprising a support layer to support the layer of continuous filament fibers, wherein the support layer is a nonwoven or a plastic film.

16. The absorbent article as claimed in claim 1, wherein the layer of continuous filament fibers comprises fibers of different material and/or different thickness.

17. An absorbent article comprising:

a layer of continuous filament fibers, which are bonded together in a bonding pattern, at least some of said fibers being thermoplastic and the bonding pattern being achieved by thermal bonding, with the bonds creating channels along the surface of the layer to allow for liquid distribution, wherein the bonding pattern comprises points, spots or lines which cross a longitudinal direction of the continuous filament fibers, and wherein different bonding lines overlap each other as seen in a transverse direction of the article, so that a main part of the filament fibers are bonded along at least a part of their length:

a liquid impervious backsheet, and an absorbent body arranged therebetween.

18. The absorbent article as claimed in claim 17, wherein the layer of continuous filament fibers has a basis weight of at least 5 g/m$^2$.

19. The absorbent article as claimed in claim 18, wherein the layer of continuous filament fibers has a basis weight of about 5 to 500 g/m$^2$.

20. The absorbent article as claimed in claim 18, wherein the layer of continuous filament fibers has a basis weight of about 5 to 200 g/m$^2$.

* * * * *